US008548822B2

(12) United States Patent
Moctezuma de la Barrera

(10) Patent No.: US 8,548,822 B2
(45) Date of Patent: Oct. 1, 2013

(54) REACTIVE WORKFLOW SYSTEM AND METHOD

(75) Inventor: José Luis Moctezuma de la Barrera, Freiburg (DE)

(73) Assignee: Stryker Leibinger GmbH & Co., KG, Freiburg (DE)

(*) Notice: Subject to any disclaimer, the term of this patent is extended or adjusted under 35 U.S.C. 154(b) by 2061 days.

(21) Appl. No.: 10/743,443

(22) Filed: Dec. 19, 2003

(65) Prior Publication Data
US 2005/0145257 A1 Jul. 7, 2005

(51) Int. Cl.
*G06Q 10/00* (2012.01)

(52) U.S. Cl.
USPC .................................................. 705/2; 705/3

(58) Field of Classification Search
USPC .................. 600/411; 606/170; 705/2–4
See application file for complete search history.

(56) References Cited

U.S. PATENT DOCUMENTS

| | | | |
|---|---|---|---|
| 5,007,936 A | 4/1991 | Woolson | 623/23 |
| 5,611,353 A | 3/1997 | Dance et al. | 128/782 |
| 5,682,886 A | 11/1997 | Delp et al. | 128/653.1 |
| 5,752,513 A | 5/1998 | Acker et al. | 128/653.1 |
| 5,880,976 A | 3/1999 | DiGioia, III et al. | 364/578 |
| 5,954,648 A * | 9/1999 | Van Der Brug | 600/411 |
| 6,081,336 A | 6/2000 | Messner et al. | 356/375 |
| 6,205,411 B1 * | 3/2001 | DiGioia et al. | 703/11 |
| 6,514,259 B2 | 2/2003 | Picard et al. | 606/88 |
| 6,557,558 B1 | 5/2003 | Tajima et al. | |
| 6,595,997 B2 | 7/2003 | Axelson, Jr. et al. | 606/88 |
| 6,607,487 B2 | 8/2003 | Chang et al. | 600/437 |
| 2001/0012913 A1 * | 8/2001 | Iliff | 600/300 |
| 2002/0107522 A1 | 8/2002 | Picard et al. | 606/88 |
| 2002/0116067 A1 | 8/2002 | Mears et al. | 623/22.4 |
| 2002/0193797 A1 | 12/2002 | Johnson et al. | 606/79 |
| 2003/0093103 A1 * | 5/2003 | Malackowski et al. | 606/170 |
| 2003/0153829 A1 | 8/2003 | Sarin et al. | 600/426 |
| 2003/0199856 A1 | 10/2003 | Hill et al. | 606/1 |

FOREIGN PATENT DOCUMENTS

| | | |
|---|---|---|
| WO | WO 00/39576 | 7/2000 |
| WO | 04/001569 A2 | 12/2003 |
| WO | 04/001569 A3 | 12/2003 |

OTHER PUBLICATIONS

PCT Written Opinion, Appl. No. PCT/US01/02166, dated Jan. 2, 2002.
Birkfellner et al., "Evaluation and Detection of Systematic Distortions in DC-pulsed Electromagnetic Position Sensing Devices," *Elsevier Science B.V.*, 1998, pp. 927-928.
Birkfellner et al., "Systematic Distortions in Magnetic Position Digitizers," *Med. Phys.* 25 (11), pp. 2242-2248 (Nov. 1998).
Livingston et al., "Magnetic Tracker Calibration for Improved Augmented Reality Registration," *Presence*, vol. 6, No. 5, pp. 532-546 (Oct. 1997).

(Continued)

*Primary Examiner* — Robert Morgan
*Assistant Examiner* — Rajiv Raj
(74) *Attorney, Agent, or Firm* — Howard & Howard Attorneys PLLC

(57) ABSTRACT

A system and method for determining the consequent step of a multi step procedure determines the identity of components usable in the procedure. Based on the components introduced and the context of the procedure at the time the component is introduced determines a consequent step and moves to that determined consequent step.

15 Claims, 9 Drawing Sheets

(56) References Cited

OTHER PUBLICATIONS

State et al., "Superior Augmented Reality Registration by Integrating Landmark Tracking and Magnetic Tracking," Proceedings of SIG-GRAPH 96 (New Orleans, LA, Aug. 4-9, 1996). In *Computer Graphics* Proceedings, Annual Conference Series, pp. 429-438.

Birkfellner et al., "Calibration of Tracking systems in a Surgical Environment," *IEEE Tansactions on Medical Imaging*, Nov. 17, 1998, pp. 1-6.

Birkfellner et al., "Evaluation of Magnetic Position Digitizers for Computer Assisted Surgery," *Comput. Aided Surg.* 2(3/4), 225 (1997).

International Search Report dated Aug. 15, 2001, Int'l. Appl. No. PCT/US01/02166.

*Total Knee Replacement—Computer-Assisted Surgical System Uses A Calibrated Robot*, IEEE Engineering in Medicine and Biology, May/Jun. 1995 (pp. 301-306).

\* cited by examiner

REACTIVE WORKFLOW SYSTEM AND METHOD

TECHNICAL FIELD

This invention relates to expert systems and methods and particularly expert systems that are usable in a surgical environment.

BACKGROUND ART

The increased use of technology in the surgical suite has led to increased complexity for the surgeons and their staff. Surgical navigation systems allow a surgeon to locate their instruments and tools accurately relative to the patient and enable them to perform procedures with less risk of improper result. However, a surgical navigation system with a specialized workflow for a particular procedure requires the surgeon to interact with the computer system in some fashion. There have been improved wireless tools that include the ability to manipulate the computer system from a location remote from the computer keyboard or display unit. However, the surgeon must still affirmatively advance the screen through each step during the procedure.

SUMMARY OF THE INVENTION

One aspect of the present invention is a method for determining a consequent step within a multi-step procedure. The method comprises the steps of identifying a context within the procedure; then identifying a component usable in the procedure. The method then includes determining the consequent step within the procedure based on the identity of the component and the context.

Another aspect of the present invention is a system for assisting with a surgical procedure that comprises a first circuit to identify a context within a multi-step surgical procedure. The system includes a second circuit to identify a component that is usable within the procedure. Lastly, the system has a third circuit that determines a consequent step in the procedure based on the identity of the component and the context.

A still further embodiment of the present invention is a method to determine a consequent step within a multi-step surgical procedure that includes the step of determining a context within the multi-step surgical procedure. The method also includes the step of determining the identity of a surgical instrument and the step of determining the location of the surgical instrument. The method then includes the step of determining the consequent step in the procedure from the context, the identity of the instrument and the identity of the surgical instrument.

Other aspects and advantages of the present invention will become apparent upon consideration of the following detailed description.

DETAILED DESCRIPTION OF THE PREFERRED EMBODIMENTS

Figure 1:
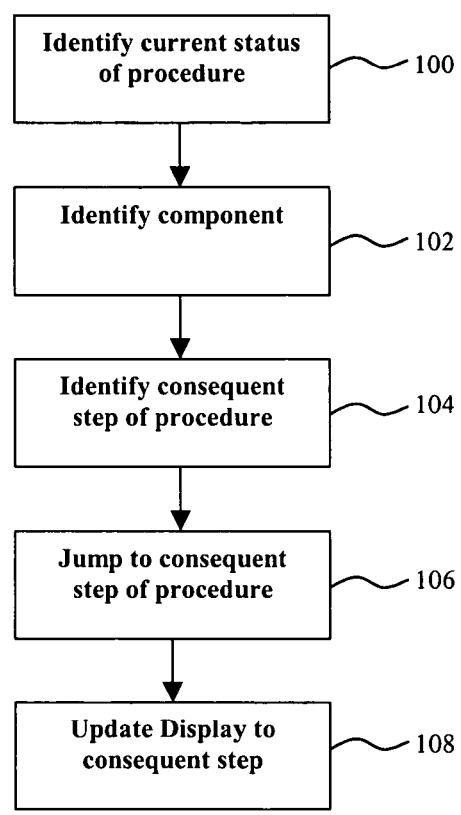
FIG. 1 is a flow diagram of one embodiment of the method and system of the present invention.

Referring to FIG. 1, the method and system begin with a block 100 that determines or identifies the current status of the procedure. For a surgical procedure as more fully discussed below or any other computer directed multi-step procedure, the block 100 will determine where in the series of display screens the process and the system is presently. With current computer controlled and directed surgical procedures, the determination can be a determination of the current state of the computer program. As an example, in a total hip replacement, the current step might be the placing of a trial implant in the prepared acetabular cup. The block 100 will know what surgical instruments or tools are needed for the current step. The system will in a block 102 identify the surgical instruments brought within the view of the surgical navigation system as discussed later. For instance, the surgeon may decide based on the trial implant that additional reaming is necessary. In this case the surgeon will introduce the cup reaming instrument into the surgical field. The block 102 will identify the reamer and also will identify the size of the particular reaming tool attached to the reamer. Based on the assessment of the particular tool, a block 104 will determine that the surgeon wants to return to the reaming display screen to assist the surgeon with the proper reaming of the acetabular cup. Once the block 104 has determined what particular step is to be performed next, a block 106 will jump directly to that point within the procedure and a block 108 will display the display screen for reaming of the acetabular cup will then be displayed and the display screen will include the correct parameters for the particular tool or tool attachment. As noted above, the automatic jumping to the correct point within a procedure will greatly assist the surgeon with their workflow and allow the surgeon to concentrate upon the surgery at hand and minimize the surgeon's interaction with the computer system. It is understood that the steps noted above will be repeated for each step through the procedure, including some step more than once, until the conclusion of the procedure at which time the system and method will terminate.

Figure 2:
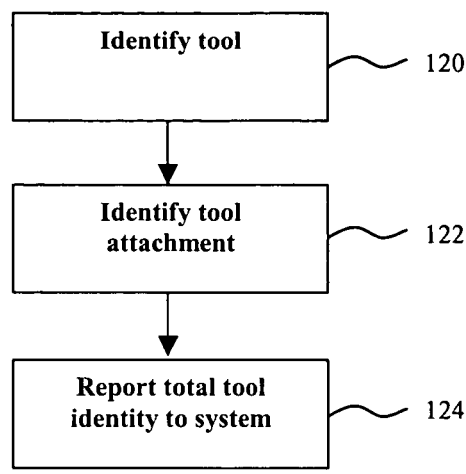
FIG. 2 is a flow diagram of one embodiment of a determination of the identity of a tool with an attachment.

In FIG. 2, a flow diagram that illustrates how a multipart tool can self identify itself and its component parts to the system. A particular method and system of this interaction uses RFID and is described in U.S. published application 2003/0093103, the disclosure of which is hereby incorporated by reference. A block 120 identifies the particular base portion of the surgical tool or instrument. This may be done in a number of conventional ways including attaching a navigation tracking device to the instrument and registering the instrument and tracker combination with the system or using RFID to identify the tool to the system. Because in most such systems, each tracking device can uniquely identify itself to the system, the system will know that a particular tool has been attached or associated with that particular tracking device. For instance, the reaming tool described above can be either attached to a particular navigation-tracking device or include built in tracking elements. When that tracking device is later located by the navigation system, the block 120 will know that the particular reaming tool has been chosen by the surgeon and has been introduced into the surgical field. A block 122 using the RFID, or other similar techniques, will identify the particular reaming cup that has been attached to the reaming tool, including the size, shape, and any other important or identifying parameters. A block 124 will then report both the identity of the reamer and the particular reaming cup to the system. The block 104 will use the identity of both the base or main tool and the particular attachment to determine what is the appropriate consequent step in the procedure.

Figure 3:
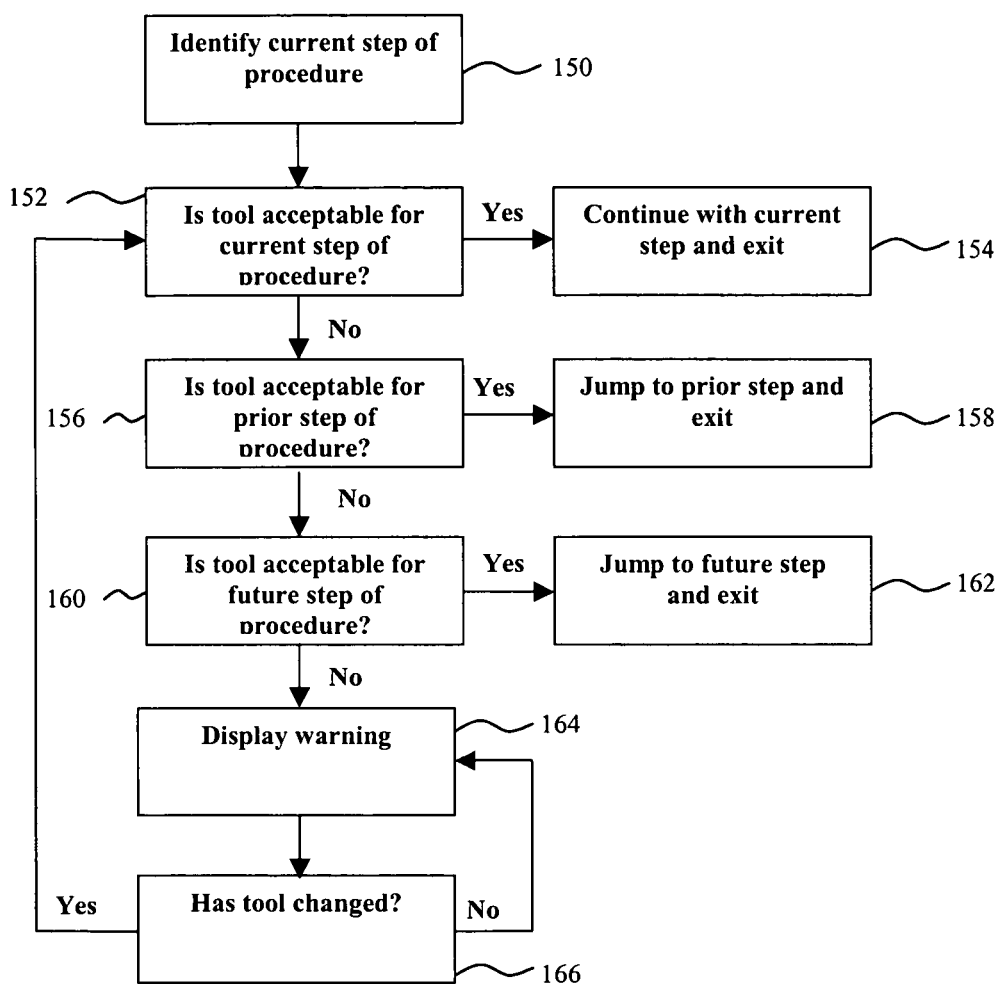
FIG. 3 is a flow diagram of detail of one way to determine the identity of the consequent step.

FIG. 3 provides more detail on one method that the block 104 can use to make the determination of the appropriate consequent step. A block 150 identifies the current step in the procedure in much the same manner as the block 100. Control then passes to a block 152 that determines if the instrument or tool that is in the surgical field and has been identified by the block 102 is acceptable for the current procedure step. If the tool is acceptable, control passes to a block 154 that continues the current step in the procedure and exits to the main routine. At the main program, the system and method will again determine the current context similar to the blocks 100 and 150. If the block 152 determines the tool is not acceptable for the current step, control will then pass to a block 156 that determines if the tool is acceptable for a prior step in the procedure. If the block 156 determines that the tool is acceptable for a prior step, the control will pass to a block 158 that jumps to the prior step that has been determined by the block 156 and the routine exits to the main program. If the block 156 determines the tool is not acceptable for a prior step, then control passes to a block 160 that queries the future steps to determine if the current tool is acceptable for a future step. If a future step is located that matches the tool, control will pass to a block 162 that jumps to the identified future step and the routine goes back to the main program. If there is no future step that is acceptable, control will pass to a block 164 that displays a warning and a block 166 queries if the tool is changed. If the identified tool has not been changed the method and system will loop back and the block 162 will continue to display the warning message. If the tool is changed, the block 164 passes control to the block 152 that starts the process over. It is also possible for the user to override the choices made by the system and to exit the routine if no acceptable tool and step combination can be found or at any other time during the process.

Figure 4:
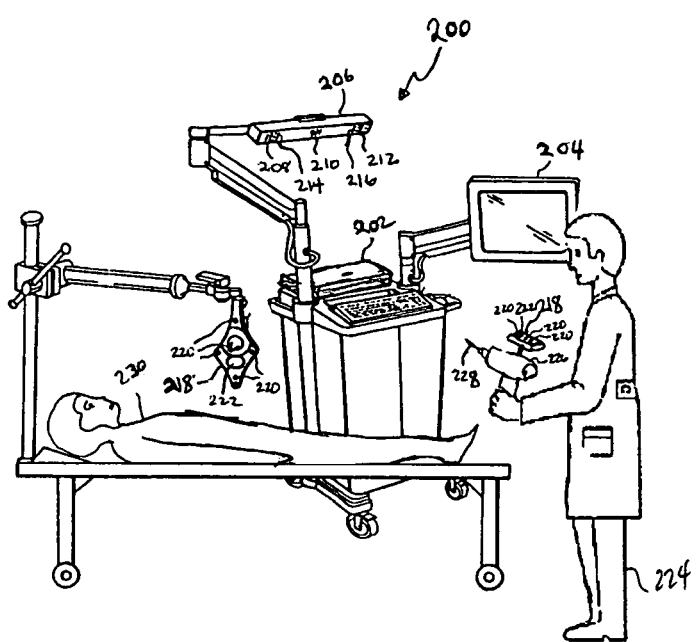
FIG. 4 is a schematic overview of a surgical navigation system that can be with an embodiment of the method and system of the present invention.

As noted previously, the method and system can be used in conjunction with a surgical navigation system 200 as shown in FIG. 4. Any type of surgical navigation system can be used such as optical, both active (LEDs) and passive (reflectors), magnetic, inertial and combination systems. Other computer-assisted systems also can be used including RFID based systems, video imaging based systems, and the like. However, for ease of description, the methods and systems of the present invention will de described using an optical active based system. The surgical navigation system 200 includes a computer 202 having internal CPU, memory and storage (not shown). The computer 202 can be any conventional computer capable or running a suitable operating system. The computer 202 will provide output and data to a display unit 204. The computer 202 is also attached to a camera 206 that includes three separate CCD arrays 208, 210 and 212. The three CCD arrays provide a three dimensional view of the operating field of the surgical navigation system 200. The camera 206 will also contain two transceivers 214 and 216. One or more tracking devices 218 are placed in the view of the camera 206.

Typically, one tracking device 218 is fixed in position to provide a reference frame for the camera 206 in the calculation of the Cartesian coordinates to locate the various devices and the tracking devices 218. The tracking device 218 has a series of LEDs 220 and each tracking device 218 has a transceiver 222 to communicate with the surgical navigation system. A typical surgical navigation system 200 is disclosed in U.S. published application 2001/0034530, the disclosure of which is hereby incorporated by reference.

When a surgeon 224 introduces a surgical tool 226 having an attachment 228, in the example as shown a drill bit, into the view of the surgical navigation system 200, the surgical navigation system will determine the current state of the procedure as described above. Using the logic such as that set out in FIG. 3, the system will jump to the appropriate display screen and configure the surgical navigation system 200 to properly display and guide the surgeon 224 to facilitate the surgeon's 224 performance of the surgical procedure. The configuration may include limiting the speed, size, temperature, pressure, or other parameter of the particular tool chosen by the surgeon 224. By moving between screens without the direct interaction from the surgeon 224 and by updating the information on those screens to reflect the choices made by the surgeon 224, the embodiment of the system and method of the present invention will provide the surgeon 224 with the benefits of computer assisted navigation and workflow but allow the surgeon 224 to work directly on a patient 230 without having to directly interact or manipulate the surgical navigation system 200.

Figure 5:
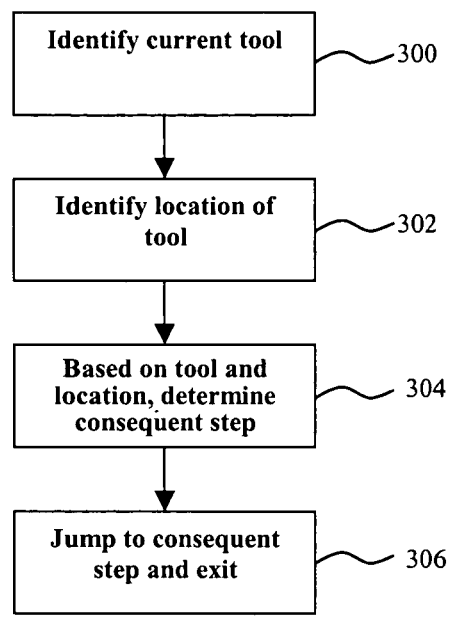
FIG. 5 is a flow diagram of a further embodiment of the method and system of the present invention.

FIG. 5 shows a further embodiment of the method and system of the present invention. In this embodiment, the system in a block 300 determined the identity of the tool or instrument as has been described previously. Then a block 302 will determine the location of the tool within the surgical field. Based on the location from the block 302 and the identity of the tool 300 and the knowledge of the current state of the procedure, the system in a block 304 will determine the consequent step and a block 306 will jump to or execute the proper consequent step. The block 306 will perform a similar procedure as shown in FIG. 3.

Figure 6:
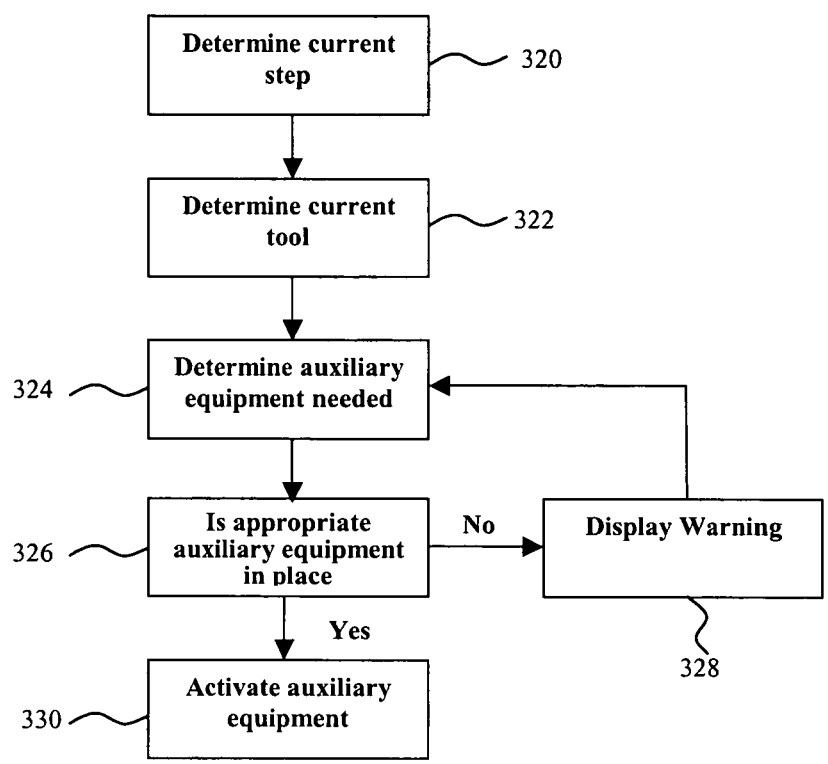
FIG. 6 is flow diagram of an alternate embodiment of the method and system of the present invention.

FIG. 6 shows a flow diagram of a system and method that allows the control of auxiliary equipment, such as operating room lighting, video and sound recording devices, suction devices, imaging devices, and the like. A block 320 determines the current status of the system as described above. Then a block 322 determines the identity of the tool or instrument also as described above. Thereafter, a block 324 determines the identity and nature of the auxiliary equipment needed. A block 326 then queries to see if the appropriate auxiliary equipment is available and connected in some fashion or interface to the surgical navigation system 200. If the auxiliary equipment is not properly connected or configured, a block 328 displays a warning message and passes control back to the block 324. If the block 326 determines that the appropriate equipment is in place and connected properly, a block 330 then activates the auxiliary equipment. An example would be if hospital policy has determined that all surgical procedures be video recorded, during the early set up portions of the procedure, the system will automatically switch on the video camera (not shown) that may be mounted on a wall or other suitable support or surface. An additional example is a suction device or tool that includes a suction feature and also is capable of being tracked by the surgical navigation system 200. As the suction device is brought into proximity to the patient 230, the block 324 will determine that the surgeon 224 needs suction. If the tool is not located near to the surgical incision, the block 326 will branch to the block 328 that will display an indication that suction is not on. As the tool is place closer to the incision location, the block 328 will pass control to the block 330 that will activate the suction.

Figure 7:
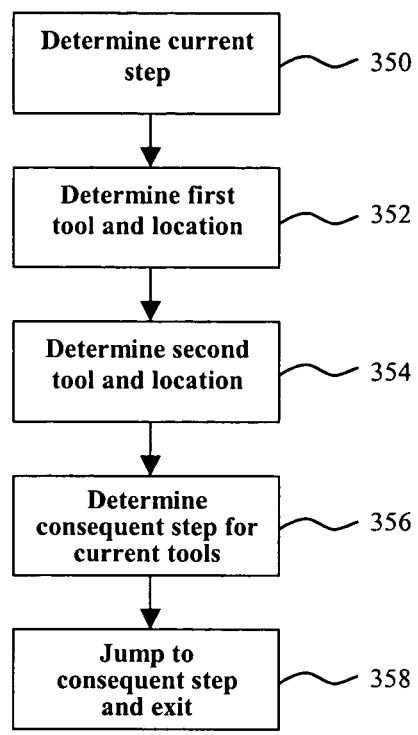
FIG. 7 is a flow diagram of a still further embodiment of the method and system of the present invention.

FIG. 7 is a flow diagram of an embodiment of the system and method of the present invention where the identification of two separate tools is detected. A block 350 determines the current state of the system or method in the same manner as described above. A block 352 then determines the location and identity of a first tool that has been introduced into the surgical field or may currently be in the surgical field. The block 352 determines the identity and location as described above using conventional navigation techniques. In a similar manner, a block 354 determines the location and identity of a second tool that has been introduced into or are present within the surgical field. Control then passes to a block 356 that determines the appropriate consequent step for the current tools and context. A block 358 then jumps to the consequent step as determined by the block 356. While FIG. 7 uses two different tools, there is no limit on the number of tools that can be identified, subject only to the maximum number of different tools or items the surgical navigation system 200 can simultaneously track.

Figure 8:
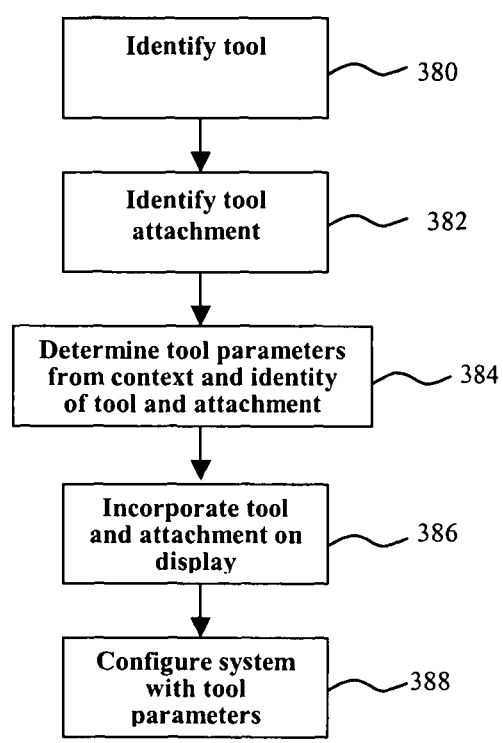
FIG. 8 is a flow diagram of an additional further embodiment of the method and system of the present invention.

FIG. 8 is a further embodiment of the method and system of the present invention. A block 380 identifies the particular tool or instrument in a manner similar to that described above. Control passes to a block 382 that identifies the attachment or accessory that is being used with the tool. Based on the identification of the tool in the block 380 and the attachment in the block 382, a block 384 determines the appropriate tool parameter or parameters also using the context of the current step in the procedure. A block 386 then will display proper tool and attachment combination on the display and a block 388 configures the surgical navigation system 200 to the particular parameters of the tool and the attachment combination.

As noted above, the system and method of the present invention have been described primarily utilizing a surgical navigation system as an example. The method and system of the present invention can also be used for a wide variety of applications where either robots or navigation systems are used. Examples include manufacturing systems, complex parts assembly processes and systems, and the like.

Also, combinations of the various embodiments can also be incorporated into a system and method for application to various situations. For instance, the system and method may identify multiple tools and also switch on a video recorder as the appropriate consequent action.

Figure 9:
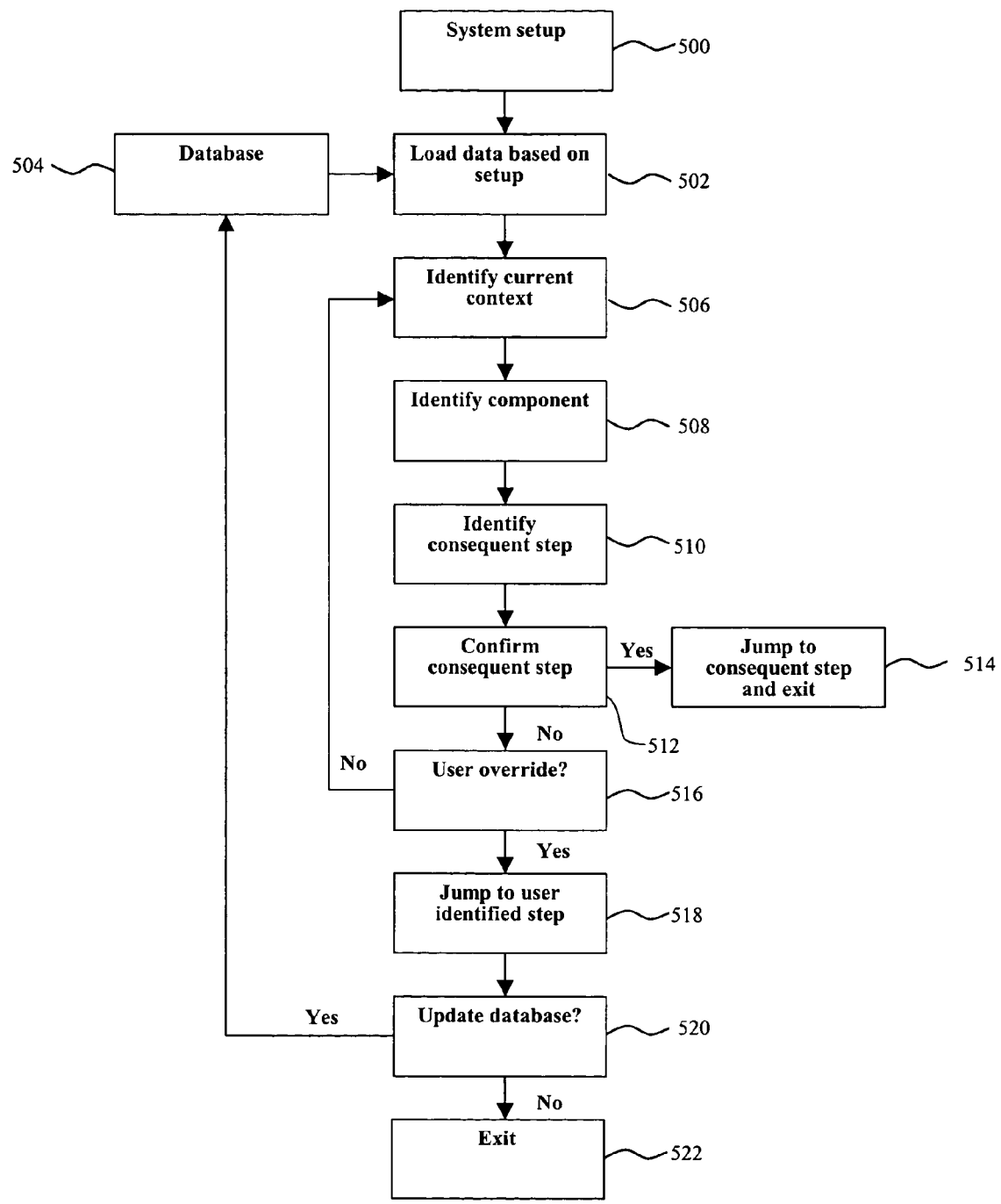
FIG. 9 is a flow diagram of another embodiment of the method and system of the present invention.

As shown in FIG. 9, the system and method may also incorporate an option for human override so that the user can direct the system and method to the consequent step desired by the user. This feature is already a function of current systems and can be incorporated into the reactive workflow system and method of the present invention as a fail-safe option. In addition, the system and method may include an option to include a screen to confirm the chosen consequent step. Further, the system and method may also provide for a learning mode that would enable the user to update the database with the particular preferences and refinements to a procedure desired by a specific user.

A block 500 sets up the system based on information entered by a user, including but not limited to the identity of the patient, the type of procedure, the identity of the surgeon or surgeons, the date and other information typically entered prior to the beginning of a surgical procedure. A block 502 then will load data from a database 504 based on the specific entries provided in the block 500. The block 502 will then configure the system to customize the system to the particular preferences of the surgical team.

A block 506 will then determine the current context. At the beginning of the procedure, it will go to the first screen as determined by the setup in the block 500. As the procedure advances through the steps, the block 506 will be the current context or step of the procedure. A block 508 identifies the component or components that have been brought within view of the system, for instance in a surgical procedure within the surgical field. A block 510 then determines the consequent step based on the current context and the components identified by the block 508. The block 510 may also use data from a database similar to the database 504.

If the user has chosen to put the system into a learning mode or has a preference to see confirmation screens, a block 512 will display a confirmation message. If the consequent step is confirmed, the control passes to a block 514 that jumps to the consequent step and exits. Also, in learning mode, the system and method will update the database 504 with the information relative to the consequent step. If the consequent step is not confirmed, control passes to a block 516 that provides for the user to indicate a consequent step. If the user does not chose to override the chosen consequent step, control will pass back to the block 506 that again begins the process of determining the consequent step. If the user indicates a consequent step at the block 516, control will pass to a block 518 that jumps to the user defined consequent step. In addition, a block 520 queries if the database 504 should be updated, in which case the database 504 will be updated to indicate that the user chosen consequent step is a potential consequent step for the context and components utilized. After the block 520, the system passes to a block 522 that exits and returns to determining the consequent step for the new context.

Numerous modifications to the present invention will be apparent to those skilled in the art in view of the foregoing description. Accordingly, this description is to be construed as illustrative only and is presented for the purpose of enabling those skilled in the art to make and use the invention and to teach the best mode of carrying out same. The exclusive rights to all modifications that come within the scope of the appended claims are reserved.

I claim:

1. A method performed by a computer navigation system of determining and displaying a consequent step of a procedure comprising a first sequence of steps, the method comprising:
   identifying a current step of the procedure;
   identifying a component usable in at least one step of the procedure;
   identifying a location of the component within a field of tracking of the computer navigation system using the computer navigation system;
   analyzing, using the computer navigation system, whether the component is acceptable for use in steps of the surgical procedure including a step other than the current step or an immediately subsequent step in the first sequence;
   determining, using the computer navigation system, the consequent step based on the location, the identity of the component, and the identity of the current step; and
   based on the determination of the consequent step, displaying a representation related to the consequent step on a display unit.

2. A method performed by a computer navigation system of determining and displaying a consequent step of a surgical procedure comprising a first sequence of steps, the method comprising:

identifying a current step of the surgical procedure;

identifying a component being tracked by the computer navigation system that is to be utilized in at least one step of the surgical procedure;

analyzing, using the computer navigation system, steps of the surgical procedure including a step other than the current step or an immediately subsequent step in the first sequence;

identifying, using the computer navigation system, the consequent step as the first step analyzed for which the component is acceptable; and automatically jumping to the consequent step and displaying a representation related to the consequent step on a display unit.

3. The method of claim 2, wherein the steps of the surgical procedure are analyzed according to a second sequence, wherein the second sequence depends upon the identity of the current step.

4. The method of claim 3, wherein the second sequence comprises analyzing the current step, analyzing a prior step after analyzing the current step, and analyzing a future step after analyzing the prior step.

5. The method of claim 3, wherein the second sequence includes every step of the surgical procedure.

6. The method of claim 2 further comprising:

tracking a position of the component within a surgical field, wherein the consequent step is identified based on the position of the component.

7. The method of claim 2, wherein the component is a multipart component capable of self-identifying composite parts of the multipart component to the computer navigation system.

8. The method of claim 7, wherein the multipart component comprises a tool with an attached device, wherein the tool can identify the attached device.

9. The method of claim 7, wherein the multipart component is a tool with an attached device, wherein the attached device is separately identifiable.

10. The method of claim 2, further comprising:

configuring the consequent step with a parameter of the component.

11. The method of claim 2, wherein the consequent step comprises a warning that the component is inappropriate for any step that is analyzed.

12. The method of claim 2, wherein the consequent step includes controlling a piece of auxiliary apparatus.

13. The method of claim 2, further comprising:

identifying a second component that is to be utilized in at least one step of the surgical procedure, wherein the determination of the consequent step is based on the identity of the component, the identity of the second component, and the identity of the current step.

14. The method of claim 2, further comprising identifying the consequent step based on a database of user preferences.

15. The method of claim 2, wherein a first representation is related to the current step and a second representation is related to the consequent step.

* * * * *

UNITED STATES PATENT AND TRADEMARK OFFICE
CERTIFICATE OF CORRECTION

| | |
|---|---|
| PATENT NO. | : 8,548,822 B2 |
| APPLICATION NO. | : 10/743443 |
| DATED | : October 1, 2013 |
| INVENTOR(S) | : José Luis Moctezuma de la Barrera |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 2187 days.

Signed and Sealed this
Tenth Day of March, 2015

Michelle K. Lee
*Deputy Director of the United States Patent and Trademark Office*